United States Patent [19]

Latenser

[11] Patent Number: 4,494,536
[45] Date of Patent: Jan. 22, 1985

[54] FOAM BOOT

[76] Inventor: John F. Latenser, 604 Ridgewood Ave., Omaha, Nebr. 68114

[21] Appl. No.: 445,908

[22] Filed: Dec. 1, 1982

[51] Int. Cl.³ .............................................. A61F 5/30
[52] U.S. Cl. .................................................... 128/153
[58] Field of Search ............... 128/149, 153, 157, 165, 128/137 R, 80 R, 89 R, 90, 87 R, 83, 82, 156

[56] References Cited

U.S. PATENT DOCUMENTS

| | | | |
|---|---|---|---|
| 3,011,494 | 12/1961 | McGowan | 128/153 |
| 3,606,884 | 9/1971 | Peter | 128/149 X |
| 3,721,237 | 3/1973 | Alessio | 128/153 X |
| 4,135,504 | 1/1979 | Spann | 128/149 X |
| 4,186,738 | 2/1980 | Schleicher et al. | 128/153 |
| 4,401,113 | 8/1983 | Incorvaia | 128/156 |

FOREIGN PATENT DOCUMENTS 1027445  7/1978  Canada ............................. 128/89 R

OTHER PUBLICATIONS

Zimfoam Dressing, Journal Bone & Joint Surgery vol. 50B, No. 2, May 1968.

Primary Examiner—John D. Yasko
Attorney, Agent, or Firm—Zarley, McKee, Thomte, Voorhees & Sease

[57] ABSTRACT

A foam boot is described which is designed for use on a variety of medical patients. The boot may be used as a padding in plaster casts or as a soft padded vascular boot or as a burn dressing. The boot may also be used as a soft padding for skin grafts and for the protection of heels and sides of feet for those patients who have impaired sensation or who are unable to turn or do not turn freely. Such as in intensive care units, in nursing homes, or in rehabilitation and spinal cord injury units. The boot is comprised of a suitable foam material and comprises a foot embracing portion having an open forward toe end designed to embrace the patient's foot. A leg embracing portion extends upwardly from the foot embracing portion and is designed for embracing the patient's lower and possibly upper leg. The foot and leg embracing portions have tapered overlapping anterior edge portions to permit the boot to be easily and efficiently positioned on the patient and to prevent an uneven thickness of the material at the overlapping portions. The boot is provided with an area of increased thickness along the back of the heel and along the outer margin of the foot and heel as well over the top of the foot and inner margin of the foot. The boot is provided with an increased thickness at the upper end of the lower leg embracing portion to provide nerve protection. The height of the leg embracing portion is greater than needed in order to permit the upper end to be cut off as required. Likewise, the length of the foot embracing portion is greater than needed to permit the forward end thereof to be cut off as required.

2 Claims, 5 Drawing Figures

FOAM BOOT

BACKGROUND OF THE INVENTION

Paralyzed patients or patients who have impaired consciousness or impaired sensations such as those patients who are in intensive care, or those patients who are unable to turn themselves or who for some reason are turned only infrequently day and night, often develop difficult to heal sores or ulcers on their heels due to unremitting pressure on the heel. Ulcers also frequently develop on the outside margin of the foot in those same patients described above since the foot tends to flop over onto its outside margin thereby creating pressure on the outside margin of the foot. Perhaps the most freqently used procedure to prevent such sores is to place fleece-lined boots or layers of foam in the form of boots and to tape, belt or otherwise secure the same to the patient's feet. However, all available boots are either: (a) insecure and tend to shift position or come off during the night; (b) poorly designed so that maximum padding is not positioned where maximum protection is needed; (c) excessively bulky so that the patient can only turn or be turned with difficulty due to the blankets and sheets becoming entangled thereby obstructing movement; (d) needlessly expensive because of design characteristics; or (e) difficult to remove or apply with accuracy and simplicity with the result that errors and pressure sores easily occur.

Secondly, in cases of fractures of the lower leg or foot, a boot cast or long leg cast is usually required. Such cast must be applied after first wrapping padding around the leg and foot with care being taken to apply additional turns of padding in those areas where pressure from the cast is known to endanger the skin or to endanger the patient by putting pressure on an important nerve with a consequent threat of paralysis resulting in foot drop.

Thirdly, following skin grafting of a leg or foot, a carefully constructed padded dressing is required which will exert exactly the desired pressure over the graft yet protect the graft from the patient's creating excessive pressure on the graft simply by the patient turning his body weight upon the graft area.

Fourthly, patients who have impaired circulation in the lower extremities often require an inexpensive exchangeable dressing for use beneath elastic support wraps such as Ace bandages or flexible inelastic support wraps such as Unna boots. This category includes patients who are in need of a support wrap to permit ambulation without the danger of skin breakdown thereby forming a vascular ulcer. This category also includes patients with recent skin grafts complicated by delayed healing secondary to poor blood supply to the graft area.

Therefore, it is a principal object of the invention to provide an improved foam boot of one-piece construction.

A further object of the invention is to provide a foam boot for use on medical patients wherein the back of the heel, the outer margin of the foot and heel, and the top of the foot are provided with an increased thickness to prevent open sores from forming regardless of the position which the patient finds himself turned or is forced to rest.

Still another object of the invention is to provide a wrap-around boot with overlapping anterior margins, the anterior edge portions of which are beveled to prevent undesirable bulging and consequent pressure points by the material itself.

Still another object of the foam boot of this invention is to provide a boot which may be cut off at either the upper end such as knee level or crotch level or at the forward (toe) end thereof to accommodate various sizes of patients or various applications.

Still another object of the invention is to provide a foam boot which does not have a seam extending upwardly on the back thereof or on the side of the heel or on the side of the foot thereby avoiding the creation of pressure in those areas where pressure must be most carefully avoided.

Still another object of the invention is to provide a foam boot which can be used as a simple, swift and efficient burn dressing in the event of mass casualties.

Still another object of the invention is to provide a foam boot which can be swiftly modified to fit any adult sized foot or length or leg or girth of leg.

Still another object of the invention is to provide a foam boot which will serve as an ideal and inexpensive simplified padding for use beneath: (1) elastic wraps; (2) flexible but inelastic wraps; and (3) rigid plaster casts or splints.

Yet another object of the invention is to provide a foam boot which is economical of manufacture and thus inexpensive to stockpile in anticipation of national emergencies such as warfare.

Yet another object of the invention is to provide a foam boot which is economical of manufacture so that it is inexpensive enough to be disposable in the event of soiling which necessarily necessitates frequent replacement or changing.

SUMMARY OF THE INVENTION

Figure 1:
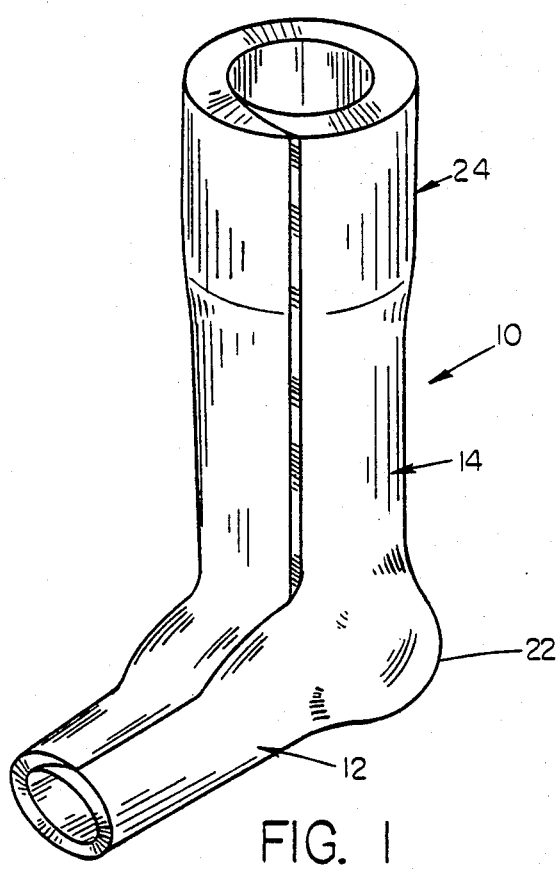
FIG. 1 is a front perspective view of the foam boot of this invention.
Figure 2:
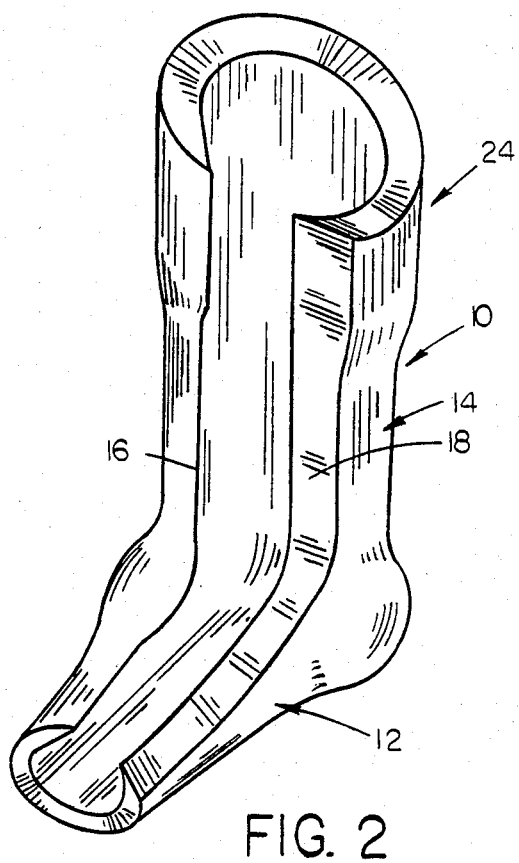
FIG. 2 is a view similar to that of FIG. 1 except that the boot has been opened to permit the patient's foot and leg to be inserted thereinto.
Figure 3:
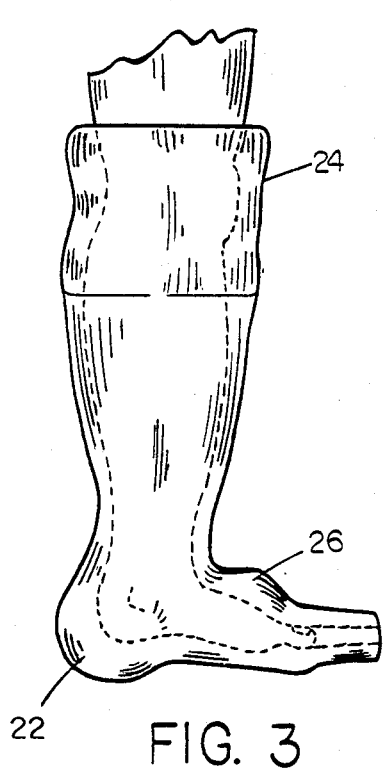
FIG. 3 is a side view of the boot mounted on a patient's leg.
Figure 4:
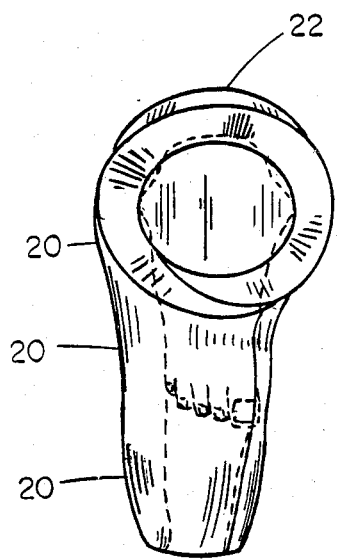
FIG. 4 is a top view of the boot.

A foam boot of unitary construction is described which may be easily placed on a patient's foot and lower leg. The boot is comprised of a foam material to provide padding for the leg and foot. The outside margins of the heel and foot are provided with increased thicknesses as is the upper end of the leg embracing portion where nerve pressure is to be avoided as in walking casts.

DESCRIPTION OF THE PREFERRED EMBODIMENT

The foam boot of this invention is referred to generally by the reference numeral 10 and is preferably constructed of a soft foam material such as urethane or the like. For purposes of description, the boot 10 will be described as comprising a foot embracing portion 12 and a leg embracing portion 14. The boot 10 is provided with overlapping edge portions 16 and 18 which are tapered as illustrated in the drawings so that undesirable bulges will be prevented when the edges 16 and 18 are overlapped. The tapered overlapping edges of the boot also permit the boot to compensate for various foot and leg thicknesses without creating undesirable bulges while still providing the necessary cushioning or padding.

Foot embracing portion 12 is provided with an area of increased thickness along the outer margin of the foot referred to generally by the reference numeral 20. Foot embracing portion 12 is also provided with a circumferential area of increased thickness at the heel referred to generally by the reference numeral 22. As seen in the drawings, the area of increased thickness 22 is seamless and provides extra or additional cushioning on all sides of the heel so that no pressure point is created at the heel thereby avoiding the formation of open sores or ulcers. In the event of extremely large and heavy extremities, a second boot may be applied over the first boot for double protection.

Figure 5:
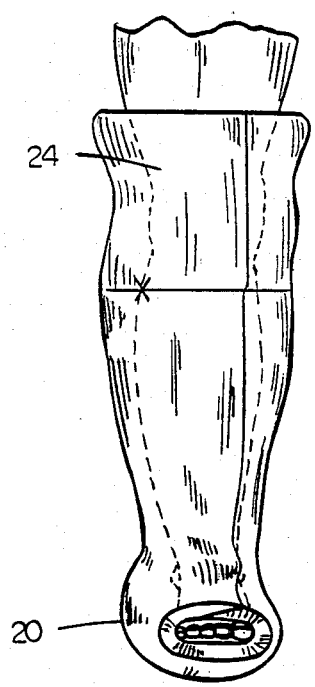
FIG. 5 is a front view of the boot mounted on a patient's leg.

The upper end of the leg embracing portion 14 is also provided with an area of increased thickness which is referred to generally by the reference numeral 24. The area of increased thickness 24 is provided for those situations wherein the upper end of a cast would be positioned therearound. The increased thickness between the patient's leg and the upper end of the cast provides additional comfort to the patient and protection against nerve damage at point "X" in FIG. 5. It should also be noted that the boot 10 is provided with an area of increased thickness over the top of the patient's foot, especially along the outer, top and inner margins, this area of thickening being referred to generally by the reference numeral 26 which provides additional cushioning in those situations where walking will occasion flexing of the forefoot with consequent cutting into the top and sides of the forefoot by the flexible inelastic overwrapping material. As seen in the drawings, the length of the foot embracing portion 12 is greater than needed and may be cut off to the desired length as required. Likewise, the height of the leg embracing portion 14 is longer than needed so that the upper end thereof may be cut off to accommodate various patient leg lengths and requirements. The material which is trimmed away or cut off is therefore available as additional padding should such be desired, e.g., over the nerve pressure area.

The boot is easily positioned on the patient's leg by simply opening up the boot so as to separate the overlapping edges 16 and 18 and allow positioning the foot and leg therein. The edges 16 and 18 would then be overlapped. The tapered or beveled configuration of the margin adjusts to a universal fit of even thickness without uneven edges as previously described. Tape or the like can then be extended across the overlapping edges (but not circumferentially around the boot as in a tourniquet) to maintain the boot snugly fitted to the patient's foot and leg.

Thus it can bee seen that if a foam boot is desired, the boot of this invention may be used and will eliminate the tedious task of cutting, beveling and fitting of foam sections into a boot and applying the same to a patient's foot and leg. It can also be seen that the boot of this invention provides additional cushioning as to prevent the formation of ulcers which normally would occur at pressure points, as when the foot flops over onto its side, as well as preventing cast pressure over vulnerable nerve pressure points.

Thus it can be seen that the invention accomplishes at least all of its stated objectives.

I claim:

1. A foam boot for use on medical patients, comprising, a foot embracing portion for embracing the patient's foot and including an open forward toe end, a leg embracing portion extending upwardly from said foot embracing portion for embracing a predetermined portion of the patient's leg, said foot and leg embracing portions being of one-piece construction, said foot and leg embracing portions being comprised of a cushion foam material, said foot and leg embracing portions having tapered overlapping edge portions to permit the boot to be closely and evenly positioned on the patient's foot and leg, said foot embracing portion having inner and outer margins, said foot embracing portion having an increased thickness along the outer margin thereof, said foot embracing portion also having a heel portion and having an increased thickness circumferentially about the heel portion thereof, said increased thicknesses providing additional cushioning for the patient's foot and heel, the height of said leg embracing portion being greater than needed to permit the upper end of said leg embracing portion to be cut off to the desired length, the length of said foot embracing portion being greater than needed to permit the forward end thereof to be cut off as required.

2. The boot of claim 1 wherein the length of said leg embracing portion is such that it will terminate below the patient's knee, said leg embracing portion having an area of increased thickness at the upper end thereof.

* * * * *